US00PP31784P2

(12) United States Plant Patent
Williams

(10) Patent No.: US PP31,784 P2
(45) Date of Patent: May 19, 2020

(54) ***ALOCASIA* PLANT NAMED 'KUCHING MASK'**

(50) Latin Name: ***Alocasia* hybrid**
Varietal Denomination: Kuching Mask

(71) Applicant: Brian Paul Williams, Louisville, KY (US)

(72) Inventor: Brian Paul Williams, Louisville, KY (US)

(73) Assignee: BRIAN'S BOTANICALS, Louisville, KY (US)

( * ) Notice: Subject to any disclaimer, the term of this patent is extended or adjusted under 35 U.S.C. 154(b) by 0 days.

(21) Appl. No.: 16/602,073

(22) Filed: Jul. 30, 2019

(51) Int. Cl.
*A01H 5/00* (2018.01)

(52) U.S. Cl.
USPC ..... Plt./373

(58) Field of Classification Search
USPC ..... Plt./373
CPC ..... A01H 5/00
See application file for complete search history.

*Primary Examiner* — Annette H Para
(74) *Attorney, Agent, or Firm* — Penny J. Aguirre

(57) ABSTRACT

A new cultivar of *Alocasia* plant named 'Kuching Mask' that is characterized by its hastate shaped foliage, its leaves that are green in color with veins that are light green in color, its plant height that averages between 2 to 2.5 m, its foliage that is held upright, its large tubers, and its resistance to root rot and cold temperatures of Zone 8 and greater.

2 Drawing Sheets

Botanical classification: *Alocasia* hybrid.
Cultivar designation: 'Kuching Mask'.

BACKGROUND OF THE INVENTION

The present invention, *Alocasia* 'Kuching Mask', relates to a new and distinct interspecific hybrid of *Alocasia*, hereinafter referred to by its cultivar name, 'Kuching Mask'. 'Kuching Mask' is a new tropical plant used as a landscape and container plant in tropical and subtropical areas.

The new cultivar was derived from a controlled breeding program conducted by the Inventor at his nursery in Louisville, Ky. The overall purpose of the breeding program is to make selections of *Alocasia* plants with large, colorful leaves that are easy to grow in the nursery and landscape. 'Kuching Mask' arose from a cross make in June of 2015 between an unnamed plant of *Alocasia longloba* x *odora* as the female parent and *Alocasia macrorrhiza* 'Borneo Giant' (not patented) as the male parent. 'Kuching Mask' was selected as a single unique plant in May of 2016 from amongst the seedlings derived from the above cross.

Asexual propagation of the new cultivar was first accomplished by tissue culture using meristematic tissue under the direction of the Inventor in April of 2017 in Eustis, Fla. Propagation by tissue culture has shown that the unique features of the new cultivar are stable and reproduced true to type in successive generations.

SUMMARY OF THE INVENTION

The following traits have been repeatedly observed and represent the characteristics of the new cultivar. These attributes in combination distinguish 'Kuching Mask' as a new and unique cultivar of *Alocasia*.

1. 'Kuching Mask' exhibits hastate shaped foliage.
2. 'Kuching Mask' exhibits leaves that are green in color with veins that are light green in color.
3. 'Kuching Mask' exhibits a plant height of 2 to 2.5 m.

4. 'Kuching Mask' exhibits foliage that is held upright.
5. 'Kuching Mask' exhibits large tubers with age.
6. 'Kuching Mask' exhibits resistance to root rot and cold temperatures of Zone 8 and greater.

The female parent of 'Kuching Mask' differs from 'Kuching Mask' in having foliage that is smaller in size and less elongated and a shorter plant size growing to only 1.2 m in height. The male parent of 'Kuching Mask', 'Borneo Giant', differs from 'Kuching Mask' in having foliage that is wider, a larger plant height of 3.6 m, cold hardiness to U.S.D.A. Zone 9, and susceptibility to root rot. 'Kuching Mask' can be most closely compared to the *Alocasia* 'Mayan Mask' (U.S. Plant Pat. No. 24,391) and plants of the species *Alocasia amazonica*. 'Mayan Mask' is similar to 'Kuching Mask' in having large green leaves with light color veins and similar cold hardiness. 'Mayan Mask' differs from 'Kuching Mask' in having a shorter plant height of 1.8 m, a dark maroon leaf color on the lower surface, tubers that are smaller in size and longer leaves. *Alocasia amazonica* is similar to 'Kuching Mask' in having hastate shaped foliage and in producing tubers. *Alocasia amazonica* differs from 'Kuching Mask' in having a much shorter plant height, leaves that are shorter in length, smaller tubers, and sensitivity to cold and wet soil which results in root rot.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Publications derived directly or indirectly from the Inventor include but are not limited to website listings by Plants Nouveau, Brian's Botanical, Farm Life Nursery, Jordan's Jungle, Turn It Tropical, and Tezuka Plants.

BRIEF DESCRIPTION OF THE DRAWINGS

The accompanying colored photographs illustrate the overall appearance and distinct characteristics of the new *Alocasia*, 'Kuching Mask'. The photographs were taken of a 2-year-old plant of 'Kuching Mask' as grown outdoors in a 10-gallon container under 6 mm poly and natural lighting in Louisville, Ky.

Figure 1:
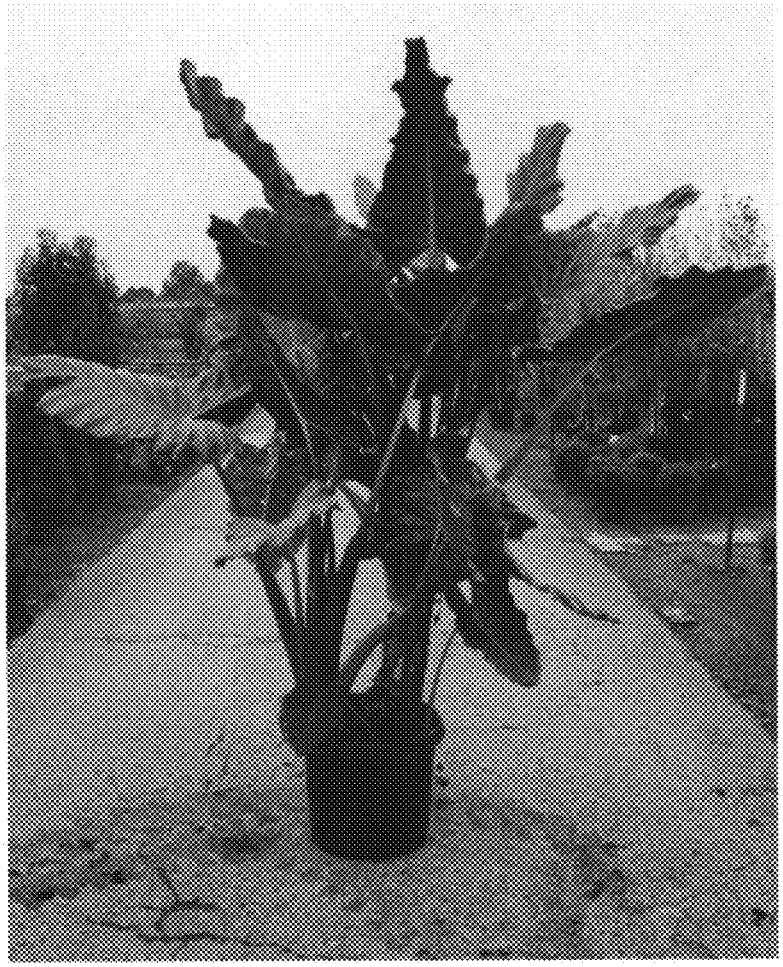
FIG. 1 provides a view of the plant habit of 'Kuching Mask'.
Figure 2:
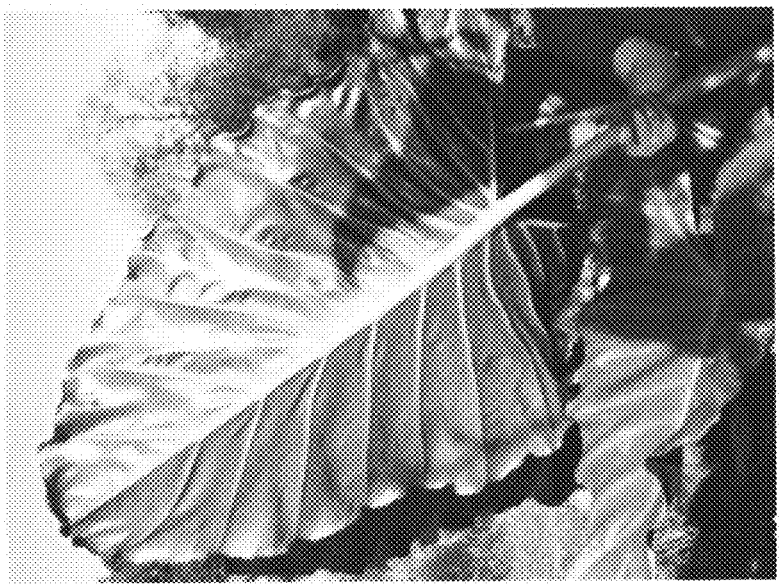

The photograph in FIG. 2 provides a close-up view of the upper surface of a leaf of 'Kuching Mask'.

Figure 3:
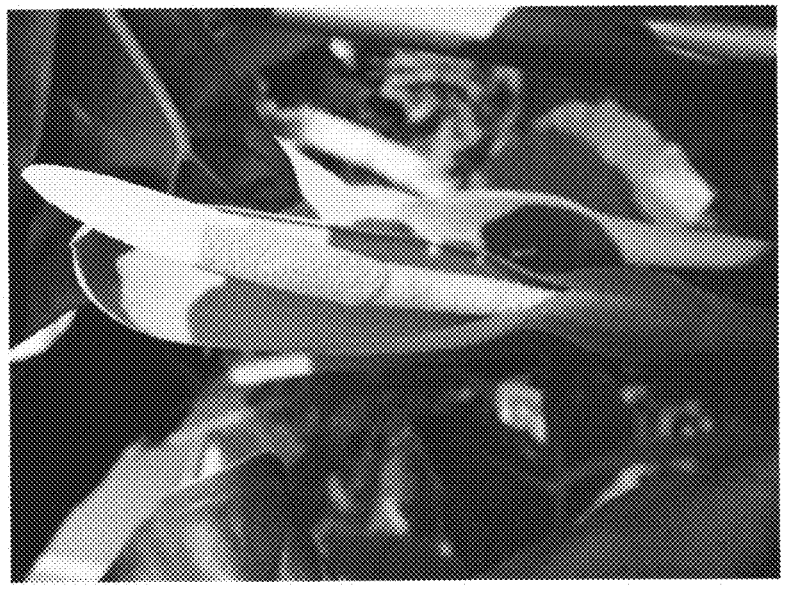

The photograph in FIG. 3 provides a close-up view of the inflorescence of 'Kuching Mask'.

The colors in the photographs are as close as possible with the photographic and printing technology utilized and the color values cited in the Detailed Botanical Description accurately describe the colors of the new *Alocasia*.

DETAILED BOTANICAL DESCRIPTION OF THE PLANT

The following is a detailed description of two-year-old plants of the new cultivar as grown outdoors in full sun under 2 mm poly greenhouse plastic in 10-gallon containers in Louisville, Ky. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Approximately 2 weeks in late summer in Kentucky.

*Plant type*.—Tropical perennial herb.

*Plant habit*.—Upright, stemless.

*Height and spread*.—Up to 2.5 m in height and 1.2 m in width at maturity.

*Cold hardiness*.—At least to U.S.D.A. Zone 8.

*Diseases and pests*.—Resistance to root rot (caused by *Pythium* spp.) has been observed.

*Roots*.—Fleshy with fibrous secondary roots, 159A in color.

*Corms*.—An average of 2 cm in length and 1.5 cm in width, comprised of scales, roughly oval in shape, 159A in color.

*Propagation type*.—Tissue culture.

*Growth rate*.—Vigorous.

*Time required for root development*.—An average of 3 to 5 weeks for root initiation with a rooted cutting produced after an average of 3 to 5 weeks.

*Stem description*.—Rhizome-like trunk (tubers) formed at the base of the petioles with age (see petiole description).

Foliage description:

*Leaf shape*.—Ovate-sagittate.

*Leaf division*.—Single.

*Leaf base*.—Sagittate, deeply cut; lobes about 10.5 cm in length and 9 cm in width.

*Leaf apex*.—Rounded with cuspidate tip.

*Leaf venation*.—Pinnate, color: young leaves upper surface 147B and lower surface a color between 150C and 150D on mid rib and 147C on lateral veins, mature leaves upper surface 137B with tinge of 144A on mid rib and lower surface a blend of 144B, 144C and 144D on mid rid rib and blending out to 146C on lateral veins, raised on both surfaces and conspicuous (more so on lower surface).

*Leaf margins*.—Undulate.

*Leaf attachment*.—Petiolate.

*Leaf arrangement*.—Emerge basally with petioles conduplicate.

*Leaf surface*.—Upper surface; slightly coriaceous, glabrous, and satiny, lower surface; slightly coriaceous, glabrous, and glossy.

*Leaf orientation*.—Held primarily upright to petiole with lobes held slightly outward.

*Leaf color*.—Emerging leaves; 144A on both surfaces, young leaves; upper and lower surface a blend of 144A and 137C, mature leaves; upper surface N137A and blending with 144A in centers between veins and lower surface 147A and blending with 147C in centers between veins.

*Leaf size*.—An average of 81 cm in length and 51 cm in width when mature.

*Leaf sinus*.—An average of 10 cm in depth and 4.5 cm in width.

*Petioles*.—Held erect to semi-erect, an average of 86 cm in length, 1 cm in distal diameter and 4.5 cm in basal diameter, glabrous, coriaceous surface, color; a blend of 147B and 147C (slightly striated) and can have slight striations of a faint N186A, rhizome-like base; about 2.5 cm in length and 3.5 cm in width, petiole scales at junction of petiole and rhizome; surface is rough and paper-like, color is a blend of 200B and N199B, base with petiole scales removed 155A with slightly tinge of 62B.

Inflorescence description:

*Inflorescence type*.—Spadix surrounded by a spathe, male portion held above female portion, only female flowers are developed.

*Inflorescence size*.—An average of 17 cm in length and 3.5 cm in width.

*Inflorescence bud*.—Linear to slightly narrow lanceolate in shape, an average of 14 cm in length and 3 cm in width, color; 144A to 144D.

*Flower fragrance*.—Slight sweet fragrance.

*Lastingness of inflorescence*.—Inflorescence blooms intermittently during the bloom period, individual flowers last about 2 to 3 weeks.

*Inflorescence/flower quantity*.—An average of 130 female flowers sessile to spadix, sessile male flowers are undeveloped.

*Spathe*.—Hooded, bract, subtending spadix, an average of 16 cm in length and 5.5 cm in width, entire margin, bottom portion; elliptic in shape, an average of 7 cm in length and 3.5 cm in width, apex fused to upper portion, truncate base, upper portion (hood); broad lanceolate in shape, an average of 12 cm in length and 5.5 cm in width, cuspidate apex, all surfaces coriaceous, glabrous, and smooth, upper and lower portion outer surface glaucescent, lower portion inner surface; dull and glabrous, color; upper portion outer and inner surface 151D, lower portion outer surface 138C and inner surface 139D and 142C near apex.

*Spadix*.—Male portion; above female zone, upright linear in shape (phallus like), apex narrowly pointed, an average of 12 cm in length and 1.3 mm in width, 159B towards the top and 158A towards the base, female portion; conical in shape, an average of 2.7 cm in length and 1.4 cm in width, 160D in color.

*Peduncle*.—Grows from base of plant, oval in shape, an average of 20 cm in length and 2 cm in diameter, durable and strong, 144D in color, coriaceous, glabrous and smooth surface.

Reproductive organs:

*Gynoecium*.—1 pistil with sessile, discoid stigmas 158B in color, monocarpous ovary is round in shape, an average of 1.5 mm in length and width, and full of many minute ovules; oval in shape, translucent and NN155C in color.

*Androecium*.—Undeveloped on plants observed, pollen was not observed.

*Fruit and seed*.—None observed.

It is claimed:

1. A new and distinct cultivar of *Alocasia* plant named 'Kuching Mask' as herein illustrated and described.

* * * * *